(12) United States Patent
Shuey

(10) Patent No.: US 8,932,622 B2
(45) Date of Patent: Jan. 13, 2015

(54) TISSUE COATING FOR PREVENTING UNDESIRED TISSUE-TO-TISSUE ADHESIONS

(75) Inventor: Steven W. Shuey, Chadds Ford, PA (US)

(73) Assignee: Actamax Surgical Materials, LLC, Berkeley, CA (US)

(*) Notice: Subject to any disclaimer, the term of this patent is extended or adjusted under 35 U.S.C. 154(b) by 1114 days.

(21) Appl. No.: 12/989,843

(22) PCT Filed: Jun. 1, 2009

(86) PCT No.: PCT/US2009/045777
§ 371 (c)(1),
(2), (4) Date: Oct. 27, 2010

(87) PCT Pub. No.: WO2009/148985
PCT Pub. Date: Dec. 10, 2009

(65) Prior Publication Data
US 2011/0045075 A1    Feb. 24, 2011

Related U.S. Application Data

(60) Provisional application No. 61/058,232, filed on Jun. 3, 2008, provisional application No. 61/058,239, filed on Jun. 3, 2008.

(51) Int. Cl.
| A61K 9/00 | (2006.01) |
| A61K 31/721 | (2006.01) |
| A61P 17/02 | (2006.01) |
| A61K 9/14 | (2006.01) |
| A61K 31/717 | (2006.01) |
| A61P 43/00 | (2006.01) |
| A61L 31/14 | (2006.01) |
| A61L 31/04 | (2006.01) |

(52) U.S. Cl.
CPC ............. *A61L 31/145* (2013.01); *A61L 31/041* (2013.01)
USPC ........... 424/426; 424/484; 424/489; 424/501; 514/57; 514/58

(58) Field of Classification Search
USPC ............... 424/426, 484, 489, 501; 514/57, 58
See application file for complete search history.

(56) References Cited

U.S. PATENT DOCUMENTS

| 4,584,188 A | 4/1986 | Graham |
| 4,636,524 A | 1/1987 | Balazs et al. |
| 4,886,787 A | 12/1989 | de Belder et al. |
| 5,017,229 A | 5/1991 | Burns et al. |
| 5,116,824 A | 5/1992 | Miyata et al. |
| 5,128,326 A | 7/1992 | Balazs et al. |
| 5,162,430 A | 11/1992 | Rhee et al. |
| 5,292,802 A | 3/1994 | Rhee et al. |
| 5,308,889 A | 5/1994 | Rhee et al. |
| 5,324,775 A | 6/1994 | Rhee et al. |
| 5,328,995 A | 7/1994 | Schaulin et al. |
| 5,356,883 A | 10/1994 | Kuo et al. |
| 5,387,752 A | 2/1995 | Scarlett et al. |
| 5,505,952 A | 4/1996 | Jiang et al. |
| 5,514,379 A | 5/1996 | Weissleder et al. |
| 5,527,893 A | 6/1996 | Burns et al. |
| 5,643,575 A | 7/1997 | Martinez et al. |
| 5,733,563 A | 3/1998 | Fortier |
| 5,760,200 A | 6/1998 | Miller et al. |
| 5,827,937 A | 10/1998 | Agerup |
| 5,906,997 A | 5/1999 | Schwartz et al. |
| 6,017,301 A | 1/2000 | Schwartz et al. |
| 6,165,488 A | 12/2000 | Tardy et al. |
| 6,235,726 B1 | 5/2001 | Burns et al. |
| 6,294,202 B1 | 9/2001 | Burns et al. |
| 6,514,534 B1 | 2/2003 | Sawhney |
| 6,521,223 B1 | 2/2003 | Calias et al. |
| 6,610,669 B1 | 8/2003 | Calias et al. |
| 6,630,457 B1 | 10/2003 | Aeschlimann et al. |
| 6,703,041 B2 | 3/2004 | Burns et al. |
| 6,831,172 B1 | 12/2004 | Barbucci et al. |
| 6,903,199 B2 | 6/2005 | Moon et al. |
| 2002/0106409 A1 | 8/2002 | Sawhney et al. |
| 2002/0192182 A1 | 12/2002 | Massia et al. |
| 2004/0101547 A1 | 5/2004 | Pendharkar et al. |
| 2004/0101548 A1 | 5/2004 | Pendharkar |
| 2005/0228433 A1 | 10/2005 | Bucay-Couto et al. |
| 2005/0260188 A1 | 11/2005 | Liu et al. |

(Continued)

FOREIGN PATENT DOCUMENTS

| JP | 1982-102932 | 6/1982 |
| JP | 1988-11167 | 1/1988 |

(Continued)

OTHER PUBLICATIONS

Pfannemuller, B., et al., "Chemical Modification of the Surface of the Starch Granules", Starch/Starke, vol. 95, No. 9, 1983, pp. 298-303.
Ferland, R., et al., "Evaluation of a Sprayable Polyethylene Glycol Adhesion Barrier in a Porcine Efficacy Model", Human Reproduction, vol. 16, No. 12, (2001), pp. 2718-2723.
Luo, Yi, et al., "Cross-Linkded Hyaluronic Acid Hydrogel Films: New Biomaterials for Drug Delivery", Journal of Controlled Release, vol. 69, (2000), pp. 169-184.
Ryan, Charlotte K., et al., "Evaluation of a Carboxymethylcellulose Sponge for Prevention of Postoperative Adhesions", The American Journal of Surgery, vol. 169, Jan. 1995, pp. 154-160.
Kirker, Kelly R., et al., "Glycosaminoglycan Hydrogel Films as Bio-Interactive Dressings for Wound Healing", Biomaterials, vol. 23, (2002), pp. 3661-3671.

(Continued)

*Primary Examiner* — Ernst V Arnold
*Assistant Examiner* — Hong Yu
(74) *Attorney, Agent, or Firm* — McCarter & English

(57) ABSTRACT

Disclosed herein are a kit and a method for forming a tissue coating that prevents undesired tissue-to-tissue adhesions resulting from trauma, surgery, infection, or other stimulus. The tissue coating is a hydrogel formed by reacting an aminocarboxymethyldextran containing primary amine groups with an oxidized carboxymethylcellulose containing aldehyde groups.

15 Claims, No Drawings

(56) References Cited

U.S. PATENT DOCUMENTS

| | | |
|---|---|---|
| 2006/0078536 A1 | 4/2006 | Kodokian et al. |
| 2006/0079599 A1 | 4/2006 | Arthur |
| 2008/0058469 A1 | 3/2008 | Abe et al. |
| 2008/0069857 A1 | 3/2008 | Yeo et al. |
| 2009/0202639 A1 | 8/2009 | Bellini et al. |

FOREIGN PATENT DOCUMENTS

| | | | |
|---|---|---|---|
| WO | WO 91/15368 | 10/1991 | |
| WO | WO 00/64977 | 11/2000 | |
| WO | WO 01/95875 A1 * | 12/2001 | ............... A61K 9/00 |
| WO | WO 02/06373 | 1/2002 | |
| WO | WO 2006/078536 | 7/2006 | |
| WO | WO 2007/120818 | 10/2007 | |

OTHER PUBLICATIONS

Rodgers, Kathleen E., et al., "Reduction of Adhesion Formation with Hyaluronic Acid After Peritoneal Surgery in Rabbits", American Society for Reproductive Medicine, Fertility & Sterility, vol. 67, No. 3, Mar. 1997, pp. 553-558.

Buckenmaier, Chester C., III, et al., "Comparison of Antiadhesive Treatments Using an Objective Rat Model", The American Surgeon, vol. 65, No. 3, Mar. 1999, pp. 274-282.

Burns, James W., et al., "A Hyaluronate Based Gel for the Prevention of Postsurgical Adhesions: Evaluation in Two Animal Species", American Society for Reproductive Medicine, Fertility & Sterility, vol. 66, No. 5, Nov. 1996, pp. 814-821.

Diamond, Michael P., "Reduction of Adhesions After Uterine Myomectomy by Seprafilm* Membrane (HAL-F): A Blinded, Prospective, Randomized, Multicenter Clinical Study", American Society for Reproductive Medicine, Fertility & Sterility, vol. 66, No. 6, Dec. 1996, pp. 904-910.

Elkins, Thomas E., et al., "Adhesion Prevention by Solutions of Sodium Carboxymethylcellulose in the Rat I." American Society for Reproductive Medicine, Fertility & Sterility, vol. 41, No. 6, Jun. 1984, pp. 926-928.

Gupta, Dimpy, et al., "Fast-Gelling Injectable Blend of Hyaluronan and Methylcellulose for Intrathecal, Localized Delivery to the Injured Spinal Cord", Biomaterials, vol. 27, (2006), pp. 2370-2379.

Ito, Taichi, et al., "Dextran-Based in situ Cross-linked Injectable Hydrogels to Prevent Peritoneal Adhesions", Biomaterials, vol. 28, (2007) pp. 3418-3426.

Ito, Taichi, et al., "The Prevention of Peritoneal Adhesions by in-situ Cross-Linking Hydrogels of Hyaluronic Acid and Cellulose Derivatives", Biomaterials, Nov. 28, No. 6, Feb. 2007, pp. 975-983.

Johns, Douglas B., et al., "Reduction of Adhesion Formation by Postoperative Administration of Ionically Cross-Linked Hyaluronic Acid", American Society for Reproductive Medicine, Fertility & Sterility, vol. 68, No. 1, Jul. 1997, pp. 37-42.

Leach, Richard E., et al., "Reduction of Postsurgical Adhesion Formation in the Rabbit Uterine Horn Model with Use of Hyaluronate/Carboxymethylcellulose Gel", American Society for Reproductive Medicine, Fertility & Sterility, vol. 69, No. 3, Mar. 1998, pp. 415-418.

Liu, Lin-Shu, et al., "Adhesion Barriers of Carboxymethylcellulose and Polyethylene Oxide Composite Gels", Journal of Biomedical Materials Research, (Appl Biomater), vol. 63, (2002), pp. 326-332.

Oelsner, Gabriel, et al., "Chondroitin Sulphate a New Intraperitoneal Treatment for Postoperative Adhesion Prevention in the Rabbit", The Journal of Reproductive Medicine, vol. 32, No. 11, Nov. 1987, pp. 812-814.

Vrijland, Wietske W., et al., "Fewer Intraperitoneal Adhesions With Use of Hyaluronic Acid-Carboxymethylcellulose Membrane", Annals of Surgery, vol. 235, No. 2, Feb. 2002, pp. 193-199.

Yeo, Yoon, et al., "In situ Cross-Linkable Hyaluronic Acid Hydrogels Prevent Post-Operative Abdominal Adhesions in a Rabbit Model", Biomaterials, vol. 27, (2006), pp. 4698-4705.

* cited by examiner

TISSUE COATING FOR PREVENTING UNDESIRED TISSUE-TO-TISSUE ADHESIONS

CROSS-REFERENCE TO RELATED APPLICATION

This application claims priority under 35 U.S.C. §119 from U.S. Provisional Application Ser. Nos. 61/058,232 and 61/058,239, filed Jun. 3, 2008.

FIELD OF THE DISCLOSURE

The disclosure relates to a kit and a method for forming a tissue coating on tissue of a living organism for preventing the formation of undesired tissue-to-tissue adhesions.

BACKGROUND

Tissue-to-tissue adhesions are attachments between tissues, organs, or other anatomical structures which are normally separate from one another. These adhesions are typically composed of fibrous bands of scar-like tissue which may form as a result of trauma, surgery, infection or other stimulus. Postsurgical adhesions resulting from abdominal, gynecological, or spinal surgeries are common and cause pain and other complications, and in some cases may require a second surgery to remove the adhesions. Various adhesion barriers have been developed to prevent or minimize the formation of these undesired tissue-to-tissue adhesions, but these barriers are either not very effective or are difficult to use. For example, preformed film barrier materials are fairly efficacious, but are difficult to handle by the surgeon. Hydrogels formed in situ by the reaction of two or more hydrogel precursors are easy to apply to the site, but these hydrogels have not proven to be very effective in preventing adhesions. Therefore, there is a need for more effective treatments for preventing undesired tissue-to-tissue adhesions caused by trauma, surgery, infection, or other stimulus, which are easy to use.

One type of hydrogel composition for inhibiting tissue adhesions is formed by reacting a carboxymethyldextran derivatized to contain hydrazide groups with a carboxymethylcellulose oxidized to contain aldehyde groups (Yeo et al., U.S. Patent Application Publication No. 2008/0069857). The hydrazide groups of the derivatized carboxymethyldextran react with the aldehyde groups of the oxidized carboxymethylcellulose to form a crosslinked hydrogel coating on the tissue. This hydrogel has been shown to be very effective in preventing post-surgical adhesions in a rabbit model, but it is very long-lasting, which may limit its clinical utility. Ideally, an adhesion prevention composition should not persist at the site once the healing process has begun, typically not longer than 1 to 3 weeks.

The problem to be solved therefore is to provide a tissue coating which is effective in preventing undesired tissue-to-tissue adhesions and which produces a hydrogel that degrades quickly, so that it does not interfere with the healing process.

SUMMARY

The stated problem is addressed herein by the discovery that a hydrogel formed by reacting a carboxymethyldextran derivatized to contain primary amine groups with a carboxymethylcellulose chemically oxidized to contain aldehyde groups is effective in preventing tissue adhesions in a rabbit model and degrades much more quickly than hydrogels formed by reacting a carboxymethyldextran chemically derivatized to contain hydrazide groups with a carboxymethylcellulose oxidized to contain aldehyde groups.

One embodiment provides a kit suitable for forming a tissue coating that is capable of preventing undesired tissue-to-tissue adhesions comprising:
a) at least one carboxymethyldextran that has been derivatized to provide at least one aminocarboxymethyldextran that contains primary amine groups, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; and
b) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons.

Another embodiment provides a dried hydrogel formed by a process comprising the steps of:
a) reacting in a solvent (i) at least one carboxymethyldextran that has been derivatized to provide at least one aminocarboxymethyldextran that contains primary amine groups, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; with (ii) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons, to form a hydrogel; and
b) treating said hydrogel to remove at least a portion of said solvent to form the dried hydrogel.

Another embodiment provides a method for forming a tissue coating that is capable of preventing undesired tissue-to-tissue adhesions comprising:
applying to an anatomical site on tissue of a living organism:
a) at least one carboxymethyldextran that has been derivatized to provide at least one aminocarboxymethyldextran that contains primary amine groups, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; followed by
b) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons;
or applying (b) followed by (a) and mixing (a) and (b) on the site; or
premixing (a) and (b) and applying the resulting mixture to the site.

Another embodiment provides a method for forming a tissue coating that is capable of preventing undesired tissue-to-tissue adhesions comprising: applying to an anatomical site on tissue of a living organism a dried hydrogel formed by a process comprising the steps of:
  a) reacting in a solvent (i) at least one carboxymethyldextran that has been derivatized to provide at least one aminocarboxymethyldextran that contains primary amine groups, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; with (ii) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons, to form a hydrogel; and
  b) treating said hydrogel to remove at least a portion of said solvent to form the dried hydrogel.

DETAILED DESCRIPTION

Disclosed herein are a kit and a method for forming a tissue coating that is capable of preventing undesired tissue-to-tissue adhesions caused by trauma, surgery, infection or other stimulus. The kit comprises at least one carboxymethyldextran that has been derivatized to contain primary amine groups and at least one carboxymethylcellulose that has been oxidized to contain aldehyde groups. When applied to the tissue site, the two components react to form a hydrogel coating, which has been shown to be effective in preventing undesired tissue adhesions in a rabbit model.

Additionally, the hydrogel is biocompatible and degrades rapidly in testing in vitro, suggesting that it will not persist at the site and interfere with the healing process.

Additionally, a dried hydrogel is provided that may also be useful in preventing undesired tissue-to-tissue adhesions.

Unless otherwise defined, all technical and scientific terms used herein have the same meaning as commonly understood by one of ordinary skill in the art to which this disclosure belongs. In case of conflict, the present specification, including definitions, will control.

The following definitions are used herein and should be referred to for interpretation of the claims and the specification.

The term "aminocarboxymethyldextran" refers to carboxymethyldextran that has been chemically derivatized to contain primary amine groups.

The term "primary amine group" refers to a neutral amino group having two free hydrogens. The amino group may be bound to a primary, secondary or tertiary carbon.

The term "oxidized carboxymethylcellulose" refers to carboxymethylcellulose that has been reacted with an oxidizing agent to introduce aldehyde groups into the molecule.

The term "equivalent weight per aldehyde group" refers to the average molecular weight of the compound divided by the number of aldehyde groups in the molecule.

The term "degree of carboxymethylation" refers to the statistical proportion of glucose units within dextran which are modified to contain a carboxymethyl group. For example, if on average each glucose unit has been modified to contain only one carboxymethyl group, the carboxymethyldextran would be said to have a degree of carboxymethylation of 1.0.

The term "primary amine substitution level" refers to the percentage of glucose units within carboxymethyldextran which are modified to contain a primary amine group. For example, if on average each glucose unit has been modified to contain only one primary amine group, the aminocarboxymethyldextran would be said to have a primary amine substitution level of 100%.

The term "preventing undesired tissue-to-tissue adhesions" means that the hydrogel tissue coating formed by reacting at least one aminocarboxymethyldextran with at least one oxidized carboxymethylcellulose, when applied prior to the formation of adhesions which may result from trauma, surgery, infection, or other stimulus, will reduce the likelihood that adhesions will form. "Preventing undesired tissue-to-tissue adhesions" does not require that the likelihood of adhesion formation is reduced to zero. Instead, "preventing undesired tissue-to-tissue adhesions" refers to a clinically significant reduction in the likelihood of adhesion formation resulting from trauma, surgery, infection or other stimulus, for example, a clinically significant reduction in the incidence or number of adhesions and/or the severity of the adhesions.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "crosslink" refers to a bond or molecular chain attached between and linking two different polymer chains.

The term "dried hydrogel" refers to a hydrogel that has been treated to remove at least a portion of the solvent contained therein. In one embodiment, substantially all of the solvent is removed from the hydrogel.

The term "% by weight" as used herein refers to the weight percent relative to the total weight of the solution or dispersion, unless otherwise specified.

The term "anatomical site" refers to any external or internal part of the body of humans or animals.

The term "tissue" refers to any tissue, both living and dead, in humans or animals.

By medical application is meant medical applications as related to humans and animals.

When an amount, concentration, or other value or parameter is given as a range, this is to be understood as specifically disclosing all ranges formed from any pair of any upper range limit and any lower range limit, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

As used herein, the terms "comprises", "comprising", "includes", "including", "containing", "characterized by", "has", "having", or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Aminocarboxymethyldextran

Aminocarboxymethyldextrans (CMDX-NH2) are derivatives of carboxymethyldextran (CMDX) that contain primary amine groups. Aminocarboxymethyldextrans may be prepared by chemical modification of carboxymethyldextrans.

Carboxymethyldextrans are derivatives of dextran, which contain carboxymethyl groups (—CH2-COOH) bound to hydroxyl groups at the 2, 3, and 4 positions on the glucose rings making up the dextran. Typically, carboxymethyldextrans are a heterogeneous mixture having a distribution of different molecular weights, and are characterized by an average molecular weight, for example, the weight-average molecular weight ($M_w$), or the number average molecular weight ($M_n$), as is known in the art. Suitable aminocarboxymethyldextrans may be prepared from carboxymethyldextrans having a weight-average molecular weight of about 1,000 to about 1,000,000 Daltons and a degree of carboxymethylation of about 0.1 to about 2.5. In one embodiment, the carboxymethyldextran has a weight-average molecular weight of about 10,000 to about 60,000 Daltons. In one embodiment, the carboxymethyldextran has a degree of carboxymethylation of about 0.9 to about 2.1.

Suitable carboxymethyldextrans are available commercially from companies such as Sigma-Aldrich (St. Louis, Mo.). Alternatively, carboxymethyldextrans can be prepared by carboxymethylation of dextrans using methods known in the art. For example, a carboxymethyldextran may be prepared by reacting dextran with chloroacetic acid, as described by Yeo et al, (copending U.S. Patent Application Publication No. 2008/0069857), and as described in General Methods herein below. Suitable dextrans have a weight-average molecular weight of about 1,000 to about 1,000,000 Daltons. The degree of carboxymethylation can be determined using methods known in the art such as by titration with standard sodium hydroxide, or using the NMR method described by Ho et al. (*Anal. Chem.* 52:916, 1980).

The aminocarboxymethyldextran can be prepared by chemical derivatization of a carboxymethyldextran to incorporate primary amine groups into the molecule using methods known in the art. For example, the carboxymethyldextran can be reacted with a mono-protected diamine, such as 1-BOC (i.e., t-butoxycarbonyl)ethylenediamine, after activation of the carboxymethyl group with a water-soluble carbodiimide, such as 1-ethyl-3-(3-dimethylaminopropyl) carbodiimide hydrochloride (EDC), as described in detail in General Methods herein below. The protecting group is chemically removed to form the aminocarboxymethyldextran having primary amine groups. Additionally, the aminocarboxymethyldextran may be prepared by reacting a carboxymethyldextran with a glycidyl amine, or by reacting a carboxymethyldextran lactone with a diamine.

The primary amine substitution level of the aminocarboxymethyldextran can be determined using methods known in the art, such as proton nuclear magnetic resonance spectroscopy (NMR). In one embodiment, the primary amine substitution level of the aminocarboxymethyldextran is about 10% to about 150%. In another embodiment, the primary amine substitution level of the aminocarboxymethyldextran is about 10% to about 75%.

Oxidized Carboxymethylcellulose

Oxidized carboxymethylcelluloses containing aldehyde groups (CMC-CHO) can be prepared by oxidation of a carboxymethylcellulose (CMC), a cellulose derivative with carboxymethyl groups (—CH2-COOH) bound to some of the hydroxyl groups of the glucopyranose rings that make up the cellulose backbone.

Typically, carboxymethylcelluloses are a heterogeneous mixture having a distribution of different molecular weights, and are characterized by an average molecular weight, for example, the weight-average molecular weight ($M_w$), or the number average molecular weight ($M_n$), as is known in the art. Suitable carboxymethylcelluloses have a weight-average molecular weight of about 5,000 to about 500,000 Daltons. In another embodiment, the carboxymethylcellulose has a weight-average molecular weight of about 50,000 to about 200,000 Daltons. Carboxymethylcelluloses having various weight-average molecular weights and degrees of carboxymethylation are available from companies such as Sigma-Aldrich. Alternatively, carboxymethylcellulose may be prepared from cellulose using methods known in the art. For example, cellulose may be derivatized with carboxymethyl groups using the method described above for the preparation of carboxymethyldextran. In one embodiment, the degree of carboxymethylation of the carboxymethylcellulose is about 0.15 to about 1.0. In another embodiment, the degree of carboxymethylation of the carboxymethylcellulose is about 0.82.

Oxidized carboxymethylcellulose may be prepared by oxidizing carboxymethylcellulose using any suitable oxidizing agent, including but not limited to, periodates, hypochlorites, ozone, peroxides, hydroperoxides, persulfates, and percarbonates. In one embodiment, the carboxymethylcellulose is oxidized by reaction with sodium periodate, for example as described by Mo et al. (*J. Biomater. Sci. Polymer Edn.* 11:341-351, 2000). The carboxymethylcellulose may be reacted with different amounts of periodate to give carboxymethylcelluloses with different degrees of oxidation and therefore, different equivalent weights per aldehyde group, as described in detail in General Methods herein below. The aldehyde content of the oxidized carboxymethylcellulose may be determined using methods known in the art. For example, the dialdehyde content of the oxidized carboxymethylcellulose can be determined using the method described by Hofreiter et al. (*Anal Chem.* 27:1930-1931, 1955), as described in detail in General Methods herein below. In that method, the amount of alkali consumed per mole of dialdehyde in the oxidized carboxymethylcellulose, under specific reaction conditions, is determined by a pH titration.

Upon oxidation of the carboxymethylcellulose, the weight-average molecular weight is reduced due to oxidative cleavage or acid hydrolysis of the carboxymethylcellulose backbone. Therefore, the oxidized carboxymethylcellulose typically has a weight-average molecular weight of about 5,000 to about 100,000 Daltons. In one embodiment the weight-average molecular weight of the oxidized carboxymethylcellulose is about 10,000 to about 40,000 Daltons. In another embodiment, the weight-average molecular weight of the oxidized carboxymethylcellulose is about 10,000 to about 30,000 Daltons. The weight-average molecular weight of the oxidized carboxymethylcellulose may be determined using methods known in the art, such as gel permeation chromatography.

In one embodiment, the equivalent weight per aldehyde group of the oxidized carboxymethylcellulose is about 125 to about 750 Daltons. In another embodiment, the equivalent weight per aldehyde group of the oxidized carboxymethylcellulose is about 180 to about 495 Daltons.

Methods for Forming a Tissue Coating

The aminocarboxymethyldextran and the oxidized carboxymethylcellulose may be used in various forms to form a coating on tissue that is capable of preventing undesired tissue-to-tissue adhesions. In one embodiment, the oxidized carboxymethylcellulose containing aldehyde groups and the aminocarboxymethyldextran containing primary amine groups are used in the form of aqueous solutions or dispersions. Dispersion, as used herein, refers to a colloidal suspension capable of reacting with a second reactant in an aqueous medium. To prepare an aqueous solution or dispersion comprising aminocarboxymethyldextran (referred to herein as the "first aqueous solution or dispersion"), at least one aminocarboxymethyldextran is added to water to give a concentration of about 5% to about 50% by weight relative to the total weight of the solution or dispersion. In one embodiment, the concentration of the aminocarboxymethyldextran in the first aqueous solution or dispersion is about 15% to about 25% by weight relative to the total weight of the solution or dispersion. Mixtures of different aminocarboxymethyldextrans, having different average molecular weights and/or different primary amine substitution levels, may also be used. If a mixture of different aminocarboxymethyldextrans is used, the total concentration of the aminocarboxymethyldextrans is about 5% to about 50% by weight relative to the total weight of the solution or dispersion. In one embodiment, the total concentration of the aminocarboxymethyldextrans in the first aqueous solution or dispersion is about 15% to about 25% by weight relative to the total weight of the solution or dispersion.

Similarly, to prepare an aqueous solution or dispersion comprising oxidized carboxymethylcellulose containing aldehyde groups (referred to herein as the "second aqueous solution or dispersion"), at least one oxidized carboxymethylcellulose is added to water to give a concentration of about 5% to about 50% by weight relative to the total weight of the solution or dispersion. In one embodiment, the concentration of the oxidized carboxymethylcellulose in the second aqueous solution or dispersion is about 15% to about 25% by weight relative to the total weight of the solution or dispersion. Mixtures of different oxidized carboxymethylcelluloses containing aldehyde groups, having different average molecular weights and/or different equivalent weights per aldehyde group, may also be used. If a mixture of different oxidized carboxymethylcelluloses is used, the total concentration of the oxidized carboxymethylcelluloses is about 5% to about 50% by weight relative to the total weight of the solution or dispersion. In one embodiment, the total concentration of the oxidized carboxymethylcelluloses in the second aqueous solution or dispersion is about 15% to about 25% by weight relative to the total weight of the solution or dispersion. The optimal concentrations of the two aqueous solutions or dispersions to be used depend on the application, and can be readily determined by one skilled in the art using routine experimentation.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, ultraviolet irradiation, or ultra-filtration through a 0.2 μm pore membrane.

The first aqueous solution or dispersion and/or the second aqueous solution or dispersion may further comprise various additives depending on the intended application. Preferably, the additive is compatible with the component of the aqueous solution or dispersion to which it is added. Specifically, the additive does not contain groups that would interfere with effective gelation of the hydrogel. The amount of the additive used depends on the particular application and may be readily determined by one skilled in the art using routine experimentation. For example, the first aqueous solution or dispersion and/or the second aqueous solution or dispersion may comprise at least one additive selected from pH modifiers, viscosity modifiers, antimicrobials, colorants, healing promoters, surfactants, pharmaceutical drugs and therapeutic agents.

The aqueous solution(s) or dispersion(s) may optionally include at least one pH modifier to adjust the pH of the solution(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution(s) or dispersion(s) may optionally include at least one thickener. The thickener may be selected from among known viscosity modifiers, including, but not limited to, polysaccharides and derivatives thereof, such as starch or hydroxyethylcellulose.

The aqueous solution(s) or dispersion(s) may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may also optionally include at least one colorant to enhance the visibility of the solution(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The aqueous solution(s) or dispersion(s) may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution(s) or dispersion(s) may optionally include at least one pharmaceutical drug or therapeutic agent. Suitable drugs and therapeutic agents are well known in the art (for example see the United States Pharmacopeia (USP), *Physician's Desk Reference* (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual,* 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; and radiolabels.

The first aqueous solution or dispersion comprising the at least one aminocarboxymethyldextran and the second aqueous solution or dispersion comprising the at least one oxidized carboxymethylcellulose may be applied to an anatomical site on tissue of a living organism in any number of ways to form a coating that is capable of preventing undesired tissue-to-tissue adhesions. Once both solutions or dispersions are applied to a site, they crosslink to form a hydrogel which coats the tissue, a process referred to herein as curing, typically in about 2 seconds to about 2 minutes.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the two aqueous solutions or dispersions are contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). Additionally, the double barrel syringe may contain a motionless mixer, such as that available from ConProtec, Inc. (Salem, N.H.) or Mixpac Systems AG (Rotkreuz, Switzerland), at the tip to effect mixing of the two aqueous solutions or dispersions prior to application. Alternatively, the mixing tip may be equipped with a spray head, such as that described by Cruise et al. in U.S. Pat. No. 6,458, 147.

In one embodiment, the two aqueous solutions or dispersions are applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the oxidized carboxymethylcellulose and the aminocarboxymethyldextran are used in the form of finely divided powders. The powders may be prepared using any suitable method. For example, the aqueous solutions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the two powders may be premixed and the resulting mixture applied to the site using the methods described above. The powders may be hydrated on the site by the addition of a suitable buffer (e.g., phosphate-buffered saline) or by the physiological fluids present at the site.

In another embodiment, the oxidized carboxymethylcellulose and the aminocarboxymethyldextran are used in the form of a dried hydrogel. In this embodiment, a hydrogel is prepared by mixing a solution or dispersion comprising at least one oxidized carboxymethylcellulose with a solution or dispersion comprising at least one aminocarboxymethyldextran to form a hydrogel. The solutions or dispersions may be prepared in any suitable solvent, including but not limited to, water, ethanol, isopropanol, tetrahydrofuran, hexanes, polyethylene glycol, and mixtures thereof. In one embodiment, the solvent is water. The solutions or dispersions may further comprise various additives depending on the intended application. Any of the additives described above may be used. The hydrogel is then treated to remove at least a portion of the solvent contained therein to form the dried hydrogel. In one embodiment, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above.

In one embodiment, the dried hydrogel is used in the form of a film. The dried hydrogel film may be formed by casting a mixture of the two aqueous solutions or dispersions on a suitable substrate and treating the resulting hydrogel to form a dried hydrogel film. The dried hydrogel film may be applied directly to an anatomical site.

In another embodiment, the dried hydrogel is used in the form of finely divided particles. The dried hydrogel particles may be formed by comminuting the dried hydrogel using methods known in the art, including, but not limited to, grinding, milling, or crushing with a mortar and pestle. The dried hydrogel particles may be applied to an anatomical site in a variety of ways, such as sprinkling or spraying.

Kits

Some embodiments provide a kit comprising at least one oxidized carboxymethylcellulose containing aldehyde groups and at least one aminocarboxymethyldextran containing primary amine groups, as described above.

In one embodiment, the kit comprises at least one oxidized carboxymethylcellulose and at least one aminocarboxymethyldextran in the form of aqueous solutions or dispersions, as described above. Each of the aqueous solutions or dispersions may be contained in any suitable vessel, such as a vial or a syringe barrel.

In another embodiment, the kit comprises at least one oxidized carboxymethylcellulose and at least one aminocarboxymethyldextran in the form of finely divided powders, as described above. The powders may be contained in separate containers or they may be premixed and contained in a single container. The kit may also comprise a buffer solution for hydrating the powders.

In another embodiment, the kit comprises a dried hydrogel formed by reacting at least one oxidized carboxymethylcellulose with at least one aminocarboxymethyldextran, as described above. The dried hydrogel may be in the form of a film, finely divided particles, or other dried forms. The kit may further comprise a buffer for hydrating the dried hydrogel. The dried hydrogel particles may be contained in any suitable container.

EXAMPLES

Various embodiments are further defined in the following Examples. It should be understood that these Examples, while demonstrating various embodiments, are given by way of illustration only. From the above discussion and these Examples, one skilled in the art can ascertain the essential characteristics of this disclosure, and without departing from the spirit and scope thereof, can make various changes and modifications to adapt it to various uses and conditions.

The meaning of abbreviations used in the Examples is as follows: "min" means minute(s), "h" means hour(s), "s" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "meq" means milliequivalent(s), "wt %" means percent by weight, "mol %" means mole percent, "M" means molar concentration, "Vol" means volume, "v/v" means volume per volume, "Da" means Daltons, "kDa" means kiloDaltons, "mw" means molecular weight, "MWCO" means molecular weight cut-off, "kPa" means kilopascals, "$^1$H NMR" means proton nuclear magnetic resonance spectroscopy, "ppm" means parts per million, "PBS" means phosphate-buffered saline, "rpm" means revolutions per minute, "CMDX" means carboxymethyldextran, "CMDX-NH2" means carboxymethyldextran modified to contain primary amine groups, "CMDX-ADH" means carboxymethyldextran modified to contain hydrazide groups, "CMC" means carboxymethylcellulose, "CMC-CHO" means carboxymethylcellulose oxidized to contain aldehyde groups, "GPC" means gel permeation chromatography, "diafiltration" and "diafiltered" refer to the removal of small molecules from a solution by alternating ultrafiltration and redilution, or continuous ultrafiltration and dilution to maintain constant volume.

A reference to "Aldrich" or a reference to "Sigma" means the said chemical or ingredient was obtained from Sigma-Aldrich, St. Louis, Mo.

All water used in the following Examples was purified using a Millipore Nanopure™ water purification system (Millipore Corp., Bedford, Mass., unless otherwise stated.
General Methods:
Preparation of Carboxymethyldextrans:

Preparation of 60 kDa Carboxymethyldextran with Degree of Carboxymethylation of 2.18 (CMDX-60-2.18)

To a 1-L, 3-neck round bottom flask equipped with a thermometer, a condenser and a 250 mL addition funnel, was added a solution consisting of 25 g of dextran having an average molecular weight of 60 to 90 kDa (Sigma) in 250 mL of water. To this solution was added 75.5 g of chloroacetic acid (Aldrich) with magnetic stirring. The resulting solution was placed in an ice bath and treated over 15 min with portions of NaOH with a total weight of 60 g, resulting in a faint yellow solution. The reaction mixture was then placed in an oil bath and heated to 70° C. for 3 h. The reaction mixture was cooled and quickly brought to pH 2.5 by addition of 6 N HCl. An additional 300 mL of water was added and the reaction mixture was diafiltered using a Millipore Pellicon II TFF system (Millipore Corp., Billerica, Mass.) using three 0.1 m$^2$, 1 kDa MWCO filters in series. The collected permeate was constantly replaced with water until 5 volumes (3.5 L) of permeate had been collected. The volume was then reduced to 300 mL by continued filtration while not replacing the filtrate. The retentate was then removed and the line washed with 200 mL of water. The combined retentates were lyophilized to give 29.1 g of a fluffy white powder. The entire procedure was then repeated four more times, each time starting with the product of the previous run, to give 18.4 g of fluffy white powder.

The degree of carboxymethylation was determined using the NMR method described by Ho et al., *Anal. Chem.* 52:916 (1980), which gave a degree of carboxymethylation of 2.18. This carboxymethyldextran product is referred to herein as CMDX-60-2.18.

$^1$H NMR δ 5.0-5.1H-1 (C2 substituted) δ 5.8-4.9H-1 (C2 unsubstituted) combined 1H. δ 3.3-4.4, broad mult, combined 11H.

Preparation of 10 kDa Carboxymethyldextran with Degree of Carboxymethylation of 0.90 (CMDX-10-0.90)

To a solution containing 20 g of dextran having an average molecular weight of 8,500 to 11,500 Da (Sigma) in 165 mL of 6 N NaOH at 0° C. was added 41 g of chloroacetic acid. The temperature of the solution was then raised to 60° C. for 20 min while stirring the solution. The mixture was rapidly cooled and neutralized to pH 7.0 with 6 N HCl. The product was precipitated by slow addition of the reaction solution to 1.0 L of methanol with vigorous stirring. The white solid was collected by filtration and dried in a vacuum oven at 80° C. overnight to yield 30.1 g of product. The degree of carboxymethylation was determined by the method of Ho et al., supra to be 0.90. This carboxymethyldextran product is referred to herein as CMDX-10-0.90.

$^1$H NMR δ 5-O-5.2 mult. 1H, δ 3.4-4.3 mult 7.5H.

Preparation of 60 kDa Carboxymethyldextran with Degree of Carboxymethylation of 0.91 (CMDX-60-0.91)

To a solution containing 20 g of dextran having an average molecular weight of 60 to 90 kDa (Sigma) in 165 mL of 6 N NaOH at 0° C. was added 41 g of chloroacetic acid. The temperature of the solution was then raised to 60° C. for 20 min while stirring the solution. The mixture was rapidly cooled and neutralized to pH 7.0 with 6 N HCl. The product was precipitated by slow addition of the reaction solution to 1.0 L of methanol with vigorous stirring. The white solid was collected by filtration, resuspended in 200 mL of water and re-precipitated. The resulting solid was dried in a vacuum oven at 80° C. overnight to yield 27.6 g of white powder. The degree of carboxymethylation was determined by the method of Ho et al., supra to be 0.91. This carboxymethyldextran product is referred to herein as CMDX-60-0.91.

$^1$H NMR δ 5.0-5.2 mult. 1H, δ 3.4-4.3 mult 9.9H.

Preparation of 10 kDa Carboxymethyldextran with Degree of Carboxymethylation of 1.78 (CMDX-10-1.78)

The 10 kDa carboxymethyldextran with degree of carboxymethylation of 0.90 (CMDX-10-0.90), described above, (15 g) was dissolved in 124 mL of 6 N NaOH and cooled to 0° C. in an ice bath. The cooled solution was stirred while 30.75 g of chloroacetic acid was added, and the resulting mixture was heated to 60° C. for 20 min. The solution was rapidly cooled and pH adjusted to 7.0 by addition of concentrated HCl. The resulting solution was precipitated twice from methanol and dried in a vacuum oven at 60° C. overnight to give 16.9 g of a white solid. The solid thus obtained was dissolved in 140 mL of 6 N NaOH and cooled to 0° C. This solution was treated with 34.5 g of chloroacetic acid and then heated to 60° C. for 20 min. After cooling and neutralization with concentrated HCl, the solution was diafiltered as described above using a Millipore Pellicon II TFF system. A total of 6 volumes of permeate were collected while continuously adding water to maintain a constant retentate volume. The retentate was then collected and lyophilized to give 15.65 g of a fluffy white solid. The degree of carboxymethylation was determined by the method of Ho et al., supra to be 1.78.

This carboxymethyldextran product is referred to herein as CMDX-10-1.78.

$^1$H NMR δ 4.9-5.2 mult. (1H), 3.4-4.4 mult (9.2H).

Preparation of 60 kDa Carboxymethyldextran with Degree of Carboxymethylation of 1.80 CMDX-60-1.80)

The 60 kDa carboxymethyldextran with degree of carboxymethylation of 0.91 (CMDX-60-0.91) described above, (13 g) was dissolved in 107 mL of 6 N NaOH and cooled to 0° C. in an ice bath. The cooled solution was stirred while 26.6 g of chloroacetic acid was added, and the resulting mixture was heated to 60° C. for 20 min. The solution was rapidly cooled and pH adjusted to 7.0 by addition of concentrated HCl. The product was isolated by precipitation from methanol twice, followed by drying in a vacuum oven at 60° C. overnight. The degree of carboxymethylation was further increased by repeating the procedure with this product by dissolving 14.8 g in 122 mL of 6 N NaOH and cooling to 0° C. in an ice bath. The cooled solution was stirred while 30.31 g of chloroacetic acid was added, and the resulting mixture was heated to 60° C. for 20 min. The solution was rapidly cooled and pH adjusted to 7.0 by addition of concentrated HCl. The solution was diafiltered as described above using a Millipore Pellicon II TFF system. A total of 6 volumes of permeate were collected while continuously adding water to maintain a constant retentate volume. The retentate was then collected and lyophilized to give 14.25 g of a fluffy white solid. The degree of carboxymethylation was determined by the method of Ho et al., supra to be 1.80. This carboxymethyldextran product is referred to herein as CMDX-60-1.80.

$^1$H NMR δ 4.9-5.2 mult. (1H), 3.4-4.4 mult (9.5H).

Preparation of Aminocarboxymethyldextrans:

Preparation of 60 kDa Aminoethylamido-Carboxymethyldextran Having a Degree of Carboxymethylation of 1.36 and a Primary Amine Substitution Level of 50.2% (CMDX-NH2-60-1.36-50.2)

To a 500-mL round bottom flask was added 2 g of 60 kDa carboxymethyldextran having a degree of carboxymethylation of 1.36 (CMDX-60-1.36), prepared as described above, and 134 mL of a 1:1 mixture of dimethylformamide (DMF) and 10 mM aqueous N,N,N'N', tetramethylethylene diamine (TMED) buffer, pH 4.7. To the resulting solution was added 6.97 g of 1-ethyl-3-(3-dimethylaminopropyl) carbodiimide hydrochloride (EDC), obtained from Sigma, followed by 4.19 g of N-hydroxysuccinimide (NHS), obtained from Aldrich. The resulting mixture was stirred at room temperature under a nitrogen atmosphere for 90 min. Then, 5.83 g of 1-BOC-ethylenediamine (Combi-Blocks Inc., San Diego, Calif.) was added and the reaction mixture was stirred overnight. The solution was then diafiltered using a Millipore Pellicon II TFF system, as described above, while constantly replacing the permeate until 5 volumes of permeate had been collected. The retentate was lyophilized to give a white powder. The white powder was then re-subjected to the reaction conditions using the same amounts of reagents. Purification again was achieved by diafiltration using the Pellicon II TFF system, as described above. Lyophilization yielded 2.1 g of a white fluffy solid.

The BOC protecting group was removed using the following procedure to give the aminoethylamido-carboxymethyldextran. The white solid product (2.1 g) was treated with 30 mL of 70% aqueous trifluoroacetic acid (TFA) for 2 h, then diluted with 200 mL of water and pH adjusted to 8.0 with 6 N NaOH. The solution was diafiltered using a Millipore Pellicon II system, as described above, replacing the permeate with 0.01 M HCl until 5 volumes of permeate had been collected. Then, diafiltration was continued while replacing the next 5 volumes with 0.1 M NaCl, and then by an additional 5 volumes with water. Finally, the pH was adjusted to 8.0 with 6 N NaOH and filtration was continued until the permeate was pH 7.0. The sample was lyophilized to give 1.6 g of a white powder.

The primary amine substitution level was determined to be 50.2% using $^1$H NMR. The relative integration of the anomeric protons between 4.8 and 5.1 ppm and the methylene group adjacent to the primary amine group of the added side chain at 2.5 ppm was used to determine the level of substitution. This aminoethylamido-carboxymethyldextran is referred to herein as CMDX-NH2-60-1.36-50.2.

Preparation of 10 kDa Aminoethylamido-Carboxymethyldextran Having a Degree of Carboxymethylation of 0.90 and a Primary Amine Substitution Level of 19% (CMDX-NH2-10-0.90-19)

To a 1-L, 3-neck flask was added 5.0 g of 10 kDa carboxymethyldextran having a degree of carboxymethylation of 0.90 (CMDX-10-0.90), prepared as described above, and 335 mL of a 1:1 mixture of 10 mM TMED buffer (pH 4.7) and DMF. The mixture was stirred for 5 min to form a clear solution having a pH of 4.84. The pH of the solution was adjusted to 4.7 with 0.1 M HCl and 17.4 g of EDC was added, followed by 10.46 g of NHS. The reaction mixture was stirred under nitrogen for 2.5 h, after which time the pH dropped to 3.45. To the mixture was added a total of 14.56 g of 1-BOC-ethylenediamine in portions over 2 h while adjusting the pH so that it did not exceed a value of 4.7. Initially, the pH increased upon addition of BOC-ethylenediamine, and then dropped steadily as the reaction progressed. After the addition was completed, the pH was raised to 6.5 using 0.25 N NaOH solution. The reaction mixture was then stirred magnetically at room temperature overnight. Then the reaction mixture was transferred to a 1-L glass jar and diluted to 1.0 L with water. The volume was reduced to 400 mL using the Millipore Pellicon II system described above. Filtration was continued while continuously replacing the permeate with water until 5× the original volume had been collected (i.e., 2.0 L). The pH of the solution was adjusted from 6.35 to 3.0 using dilute HCl, then diafiltered further while replacing permeate with 0.001 M HCl solution until a total of 2.0 L of permeate was collected. The pH of the solution was adjusted from 3.4 to 7.0, then diafiltered again while replacing the permeate with water. The final solution was reduced to a volume of 300 mL. The retentate was then lyophilized to give 6.2 g of white solid.

The BOC protecting group was removed using the following procedure to give the aminoethylamido-carboxymethyldextran. The solid product (6.1 g) was transferred to a 100-mL glass jar and 40 mL of a 70:30 mixture of trifluoroacetic acid and water was added. The mixture was stirred on rotary shaker for 2 h, after which the solution was transferred to a 250-mL glass jar and diluted with 100 mL of water. The pH was adjusted from 1.3 to 7.0 using 1.0 N NaOH. The reaction mixture was diafiltered using the Millipore Pellicon II system, removing 5× the original volume through permeate while adding 0.01 M HCl as replacement. The diafiltration was then continued collecting an additional 5× volume of permeate while replacing with water. The pH of the solution was adjusted to 8.80 with 1.0 N NaOH and the solution was diafiltered and replenished with water until the pH of the permeate was between 6.0 and 7.0. The sample was then lyophilized to give 5.32 g of a dry powder. The level of primary amine substitution of the product was determined to be 19% using $^1$H NMR in $D_2O$, as described above. This aminoethylamido-carboxymethyldextran is referred to herein as CMDX-NH2-10-0.90-19.

Preparation of 60 kDa Aminoethylamido-Carboxymethyldextran Having a Degree of Carboxymethylation of 0.91 and a Primary Amine Substitution Level of 15% (CMDX-NH2-60-0.91-15)

To a 1-L, 3-neck flask was added 5.0 g of 60 kDa carboxymethyldextran having a degree of carboxymethylation of 0.91 (CMDX-60-0.91), prepared as described above, and 335 mL of a 1:1 mixture of 10 mM TMED (pH 4.7) and DMF. The mixture was stirred for 5 min to form a clear solution and then 17.4 g of EDC was added, followed by 10.46 g of NHS. The solution was stirred under nitrogen for 2 h, after which time the pH dropped to 3.45. To the solution was then added 1-BOC-ethylenediamine (14.57 g) in portions over a 2.5 h period at a rate at which the pH did not exceed 4.7. The pH of the reaction mixture initially increased upon addition of the BOC-amine, and then decreased slightly after stirring for a few minutes. When the addition was completed, the final pH was 5.63. Then, 0.25 N NaOH was added to raise the pH to 6.5. The reaction mixture was stirred magnetically at room temperature overnight. Then, the reaction mixture was transferred to a 1-L glass jar and diluted to 1.0 L with water. The volume was reduced to 400 mL using the Millipore Pellicon II system described above. The solution was then diafiltered using water to replace the collected permeate until 5× the starting volume had been collected. An additional 5× volume was collected after adjusting the pH to 3.0 with dilute HCl and replacing the permeate with 0.001 M HCl. The retentate solution was then adjusted to pH 7.0 and diafiltered, collecting an additional 5× permeate volume with replacement by water. The final retentate solution was reduced to 300 mL, then the lines were washed with 200 mL of water. The combined retentate was lyophilized to give a white powder.

The BOC protecting group was removed using the following procedure to give the aminoethylamido-carboxymethyldextran. The white powder was dissolved in 40 mL of a 70:30 mixture of trifluoroacetic acid and water, and the resulting mixture was stirred on rotary shaker for 2 h. Then, the mixture was diluted with water to 450 mL and the pH was adjusted to 7.0 with NaOH solution. The reaction mixture was diafiltered using the Millipore Pellicon II system, removing 5× the original volume through permeate while adding 0.001 M HCl as replacement. This process was repeated using water to replace the permeate. The pH was adjusted to 11.0 with 6 N NaOH, followed by continued diafiltration while replacing permeate with water until the permeate pH was about 8.0. The collected retentate solution was lyophilized to give 5.4 g of white solid. The amine substitution level of the product was determined to be 15% using $^1$H NMR in $D_2O$, as described above. This aminoethylamido-carboxymethyldextran is referred to herein as CMDX-NH2-60-0.91-15.

Preparation of 10 kDa Aminoethylamido-Carboxymethyldextran Having a Degree of Carboxymethylation of 1.78 and a Primary Amine Substitution Level of 13% (CMD-NH2-10-1.78-13)

To a 1-L, 3-neck flask was added 5.0 g of 10 kDa carboxymethyldextran having a degree of carboxymethylation of 1.78 (CMDX-10-1.78), prepared as described above, and 335 mL of a 1:1 mixture of 10 mM TMED (pH 4.7) and DMF. The mixture was stirred for 5 min to form a clear solution and then 17.4 g of EDC was added, followed by 10.46 g of NHS. The solution was stirred under nitrogen for 2.5 h, after which time the pH dropped to 3.45. To the solution was then added 1-BOC-Ethylenediamine (14.57 g) in portions over a 2.5 h period at a rate at which the pH did not exceed 4.7. The pH of the reaction mixture initially increased upon addition of the BOC-amine, and then decreased slightly after stirring for a few minutes. When the addition was completed, the final pH was 5.63. Then, 0.25 N NaOH was added to raise the pH to 6.5. The reaction mixture was stirred magnetically at room temperature overnight. Then, the reaction mixture was transferred to a 1-L glass jar and diluted to 1.0 L with water. The volume was reduced to 400 mL using the Millipore Pellicon II system described above. The solution was then diafiltered using water to replace the collected permeate until 5× the starting volume had been collected. An additional 5× volume was collected after adjusting the pH to 3.0 with dilute HCl and replacing the permeate with 0.001M HCl. The retentate solution was then adjusted to pH 7.0 and diafiltered, collecting an additional 5× permeate with replacement by water. The final retentate solution was reduced to 300 mL, then the lines were washed with 200 mL of water. The combined retentate was lyophilized to give a white powder (5.56 g).

The BOC protecting group was removed using the procedure described for CMDX-NH2-60-0.91-15. The procedure gave 5.43 g of white solid. The amine substitution of the product was determined to be 13% using $^1$H NMR in $D_2O$, as described above. This aminoethylamido-carboxymethyldextran is referred to herein as CMDX-NH2-10-1.78-13.

Preparation of 60 kDa Aminoethylamido-Carboxymethyldextran Having a Degrees of Carboxymethylation of 1.8 and a Primary Amine Substitution Level of 33% (CMDX-NH2-60-1.8-33)

To a 1-L, 3-neck flask was added 5.0 g of 60 kDa carboxymethyldextran having a degree of carboxymethylation of 1.8, (CMDX-60-1.8), prepared as described above, and 335 mL of a 1:1 mixture of 10 mM TMED (pH 4.7) and DMF. The mixture was stirred for 5 min to form a clear solution, and then 17.4 g of EDC was added, followed by 10.46 g of NHS. The solution was stirred under nitrogen for 2.5 h, after which time the pH dropped to 3.45. To the solution was then added 1-BOC-ethylenediamine (14.56 g) in portions over a 2.5 h period at a rate at which the pH did not exceed 4.7. The pH of the reaction mixture initially increased upon addition of the BOC-amine, and then decreased slightly after stirring for a few minutes. When the addition was completed, the final pH was 5.63. Then, 0.25 N NaOH was added to raise the pH to 6.5. The reaction mixture was stirred magnetically at room temperature overnight. Then, the reaction mixture was transferred to a 1-L glass jar and diluted to 1.0 L with water. The volume was reduced to 400 mL using the Millipore Pellicon II system described above. The solution was then diafiltered using water to replace the collected permeate until 5× the starting volume had been collected. An additional 5× volume was collected after adjusting the pH to 3.0 with dilute HCl and replacing the permeate with 0.001M HCl. The retentate solution was then adjusted to pH 7.0 and diafiltered, collecting an additional 5× permeate with replacement by water. The final retentate solution was reduced to 300 mL, then the lines were washed with 200 mL of water. The combined retentate was lyophilized to give a white powder (5.61 g).

The BOC protecting group was removed using the procedure described for CMDX-NH2-60-0.91-15. The procedure gave 5.3 g of white solid. The amine substitution of the product was determined to be 33% using $^1$H NMR in $D_2O$, as described above. This aminoethylamido-carboxymethyldextran is referred to herein as CMDX-NH2-60-1.8-33.

Preparation of 60 kDa Aminoethylamido-Carboxymethyldextran Having a Degree of Carboxymethylation of 1.8 and a Primary Amine Substitution Level of 61% (CMDX-NH2-60-1.8-61)

To a 1-L, 3-neck flask was added 4.5 g of 60 kDa carboxymethyldextran having a degree of carboxymethylation of 1.8, (CMDX-60-1.8) prepared as described above, and 301 mL of 1:1 mixture of 10 mM TMED (pH 4.7) and DMF. The mixture was stirred for 5 min to form a clear solution and then 15.7 g of EDC was added, followed by 9.4 g of NHS. The solution was stirred under nitrogen for 2.5 h, after which time the pH dropped to 3.45. To the solution was then added 1-BOC-ethylenediamine (13.11 g) in portions over a 2.5 h period at a rate at which the pH did not exceed 4.7. The pH of the reaction mixture initially increased upon addition of the BOC-amine, and then decreased slightly after stirring for a few minutes. When the addition was completed, the final pH was 5.63. Then, 0.25 N NaOH was added to raise the pH to 6.5. The reaction mixture was stirred magnetically at room temperature overnight. Then, the reaction mixture was transferred to a 1-L glass jar and diluted to 1.0 L with water. The volume was reduced to 400 mL using the Millipore Pellicon II system described above. The solution was then diafiltered using water to replace the collected permeate until 5× the starting volume had been collected. An additional 5× volume was collected after adjusting the pH to 3.0 with dilute HCl and replacing the permeate with 0.001M HCl. The retentate solution was then adjusted to pH 7.0 and diafiltered, collecting an additional 5× permeate with replacement by water. The final retentate solution was reduced to 300 mL, then the lines were washed with 200 mL of water. The combined retentate was lyophilized to give a white powder (4.95 g).

The entire procedure was then repeated using 4.85 g of the white powder product using the same amounts of solvent, EDC and NHS, to increase the amine substitution. A white solid of 4.62 g was recovered.

The BOC protecting group was removed using the procedure described for CMDX-NH2-60-0.91-15. The procedure gave 4.5 g of white solid. The amine substitution of the product was determined to be 61% using $^1$H NMR in $D_2O$. This aminoethylamido-carboxymethyldextran is referred to herein as CMDX-NH2-60-1.8-61.

Preparation of 10 kDa Aminoethylamido-Carboxymethyldextran Having a Degree of Carboxymethylation of 1.78 and a Primary Amine Substitution Level of 73% (CMDX-NH2-10-1.78-73)

To a 1-L, 3-neck flask was added 4.5 g of 10 kDa carboxymethyldextran having a degree of carboxymethylation of 1.78, (CMDX-60-1.78), prepared as described above, and 335 mL of 1:1 mixture of 10 mM TMED (pH 4.7) and DMF. The mixture was stirred for 5 min to form a clear solution, and then 17.4 g of EDC was added, followed by 10.46 g of NHS. The solution was stirred under nitrogen for 2.5 h, after which time the pH dropped to 3.45. To the solution was then added 1-BOC-ethylenediamine (14.56 g) in portions over a 2.5 h period at a rate at which the pH did not exceed 4.7. The pH of the reaction mixture initially increased upon addition of the BOC-amine, and then decreased slightly after stirring for a few minutes. When the addition was completed, the final pH was 5.63. Then, 0.25 N NaOH was added to raise the pH to 6.5. The reaction mixture was stirred magnetically at room temperature overnight. Then, the reaction mixture was transferred to a 1-L glass jar and diluted to 1.0 L with water. The volume was reduced to 400 mL using the Millipore Pellicon II system described above. The solution was then diafiltered using water to replace the collected permeate until 5× the starting volume had been collected. An additional 5× volume was collected after adjusting the pH to 3.0 with dilute HCl and replacing the permeate with 0.001M HCl. The retentate solution was then adjusted to pH 7.0 and diafiltered, collecting an additional 5× permeate with replacement by water. The final retentate solution was reduced to 300 mL, then the lines were washed with 200 mL of water. The combined retentate was lyophilized to give a white powder (5.56 g).

The entire procedure was then repeated using 5.2 g of the white solid product using the same amounts of solvent, EDC and NHS, to increase the amine substitution. A white solid of 4.8 g was recovered.

The BOC protecting group was removed using the procedure described for CMDX-NH2-60-0.91-15. The procedure gave 5.3 g of white solid. The degree of amine substitution of the product was determined to be 73% using $^1$H NMR in $D_2O$, as described above. This aminoethylamido-carboxymethyldextran is referred to herein as CMDX-NH2-10-1.78-73.

Preparation of 60 kDa Aminohexylamido-Carboxymethyldextran Having a Degree of Carboxymethylation of 1.36 and a Primary Amine Substitution Level of 64% (CMDX-NH2-60-1.36-64)

To a 250-mL, 3-neck flask was added 1.28 g of 60 kDa carboxymethyldextran having a degree of carboxymethylation of 1.36 (CMDX-60-1.36), prepared as described above, and 85.7 mL of 1:1 mixture of 10 mM TMED buffer (pH 4.7) and DMF. The mixture was stirred for 10 min to form a clear solution, and then 4.46 g of EDC was added, followed by 2.67 g of NHS. The mixture was stirred under nitrogen for 1.5 h and then 5.03 g of N-BOC-diaminohexane (Fluka, Switzerland) was added. The reaction mixture was stirred magnetically at room temperature overnight. Then, the reaction mixture was transferred to a 250-mL glass jar using about 50 mL of water to rinse the reaction flask. When the rinses were added to the original reaction mixture, the solution turned slightly turbid. The reaction mixture was diluted to 400 mL with water, after which the solution retained a hazy white appearance. The solution was then diafiltered using water, collecting 2.0 L of permeate. The sample was then lyophilized overnight to get a solid with some water remaining. The resulting wet solids were dissolved in about 100 mL in a 500-mL, 3-neck flask and the entire procedure was repeated in 134 mL of a 1:1 mixture of 10 mM pH 4.7 TMED buffer and DMF with the same amount of reagents to obtain a higher substitution level. After stirring overnight, the reaction mixture was transferred to a glass jar and diluted with water to 400 mL. The solution was then diafiltered using water and the resulting sample was lyophilized for 72 h to give a white foamy solid (1.29 g).

The BOC protecting group was removed using the following procedure to give the aminoethylamido-carboxymethyldextran. The solid product (1.29 g) was dissolved in 30 mL of a 70:30 mixture of trifluoroacetic acid and water, and the mixture was stirred on rotary shaker for 2 h. After this time, the solution was transferred to a 250-mL glass jar and diluted with 200 mL of water. The pH of the solution was adjusted to 8.0 using 6.0 N NaOH, and then the solution was diafiltered using the Millipore Pellicon II system, with a cassette having a 1000 MWCO. A 0.01 M HCl solution was used to replace the solution collected in the permeate (pH of permeate 2.0). This process was repeated using water (5× the original volume) to replace the permeate. The pH of the product was adjusted to 8.0, followed by continued diafiltration while replacing permeate with water until the permeate pH was between 6.0 and 7.0 The resulting sample was lyophilized for 48 h to give 0.67 g of a white foam-like solid. The amine substitution of the product was determined to be 64% using $^1$H NMR in $D_2O$, as described above. This aminoethylamidocarboxymethyldextran is referred to herein as CMDX-NH2-60-1.36-64.

Preparation of Oxidized Carboxymethylcelluloses:

Preparation of Oxidized Carboxymethylcellulose Having an Average Molecular Weight of 10.4 kDa and a Dialdehyde Content of 55% (CMC-CHO-10.4-55), Equivalent Weight per Aldehyde Group of 206 Daltons To a 3-L round bottom flask containing a magnetic stir bar was added 1.0 L of water and 10.0 g of the sodium salt of carboxymethylcellulose, average molecular weight of 90 kDa (Sigma, low viscosity, degree of carboxymethylation of 0.82). The mixture was stirred for 1 h at room temperature to form a clear solution, after which time a solution of sodium periodate in water (5.29 g of sodium periodate in 70 mL of water) was added drop-wise. The flask was covered with aluminum foil and the mixture was stirred for 67 h. After this time, the reaction mixture was diafiltered using the Millipore Pellicon II system described above. The reaction solution was transferred to a 0.5 L glass bottle and diafiltered through a 1 kDa MWCO filter with continuous replacement of permeate with water until 5× the original volume had been collected as permeate. The final solution was filtered without replacement of collected permeate until 250 mL of concentrated solution remained. The lines of the filtration system were washed with 120 mL of water, which was then added back to the original solution. Lyophilization of the solution gave 8.8 g of white solid. The weight-average molecular weight of the resulting oxidized CMC was determined to be 10.4 kDa using gel permeation chromatography (GPC).

The dialdehyde content in the resulting oxidized carboxymethylcellulose was determined using the following procedure. The oxidized CMC (0.1 to 0.3 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a clear solution. The sample was removed from the bath and the flask was cooled under cold tap water for 5 min. Then 15.00 mL of 0.25 M HCl was added to the solution, followed by the addition of 50 mL of water and 1 mL of 0.2% phenolphthalein solution. This solution was titrated with 0.25 M NaOH to an endpoint determined by a color change from yellow to purple/violet. The same titration was carried out on a sample of the starting CMC to afford a background aldehyde content. The dialdehyde content, also referred to herein as the oxidation conversion or the degree of oxidation, in the oxidized CMC sample was calculated using the following formula:

$$\text{Dialdehyed Content} = \frac{(Vb - Va)_s}{W_s / M_w} - \frac{(Vb - Va)_p}{W_p / M_w} \times 100\%$$

$Vb$ = total meq of base $Va$ = total meq of acid $W$ = dry sample weight (mg)

$M_w$ = weight-average molecular weight of polysaccharide repeat unit ( = 230 for CMC with degree of substitution of 0.85 carboxymethyl groups per glucose unit)

$s$ = oxidized sample $p$ = original sample

Using this method, the dialdehyde content of the oxidized carboxymethylcellulose was determined to be 55% (equivalent weight per aldehyde group of 206 Daltons). This oxidized carboxymethylcellulose is referred to herein as CMC-CHO-10.4-55.

Preparation of Oxidized Carboxymethylcellulose Having an Average Molecular Weight of 28 kDa and a Dialdehyde Content of 23% (CMC-CHO-28-23), Equivalent Weight per Aldehyde Group of 495 Daltons To a 3-L round bottom flask containing a magnetic stir bar was added 2.0 L of water and 20.0 g of the sodium salt of carboxymethylcellulose, average molecular weight of 90 kDa (Sigma, low viscosity, degree of carboxymethylation of 0.82). The mixture was stirred for 45 min at room temperature to form a clear solution, after which time a solution of sodium periodate in water (10.58 g of sodium periodate in 158 mL of water) was added drop-wise. The flask was covered with aluminum foil and the mixture was stirred for 6.25 h. After this time, 78 mL of ethylene glycol was added to quench the reaction. The reaction mixture was dialyzed in regenerated cellulose dialysis membranes for 72 h. Lyophilization of the solution gave 8.8 g of white solid.

The weight-average molecular weight of the resulting oxidized CMC was determined to be 28 kDa using gel permeation chromatography (GPC). The dialdehyde content of the product was determined to be 23% using the method described above (equivalent weight per aldehyde group of 495 Daltons). This oxidized carboxymethylcellulose is referred to herein as CMC-CHO-28-23.

Preparation of Oxidized Carboxymethylcellulose Having an Average Molecular Weight of 20 kDa and a Dialdehyde Content of 62% (CMC-CHO-20-62), Equivalent Weight per Aldehyde Group of 183 Daltons To a 3-L round bottom flask containing a magnetic stir bar was added 1.0 L of water and 10.0 g of the sodium salt of carboxymethylcellulose average molecular weight of 90 kDa (Sigma, low viscosity, degree of carboxymethylation of 0.82). The mixture was stirred for 1 h at room temperature to form a clear solution, after which time a solution of sodium periodate in water (5.29 g of sodium periodate in 70 mL of water) was added drop-wise. The flask was covered with aluminum foil and the solution was stirred for 22 h. After this time, 78 mL of ethylene glycol was added to quench the reaction. The reaction mixture was dialyzed in regenerated cellulose dialysis membranes for 72 h. Lyophilization of the solution gave 9.2 g of white solid.

The weight-average molecular weight of the resulting oxidized CMC was determined to be 20 kDa using gel permeation chromatography (GPC). The dialdehyde content of the product was determined to be 62% using the method described above (equivalent weight per aldehyde group of 183 Daltons). This oxidized carboxymethylcellulose is referred to herein as CMC-CHO-20-62.

Preparation of Oxidized Carboxymethylcellulose Having an Average Molecular Weight of 11 kDa and a Dialdehyde Content of 60% (CMC-CHO-11-60), Equivalent Weight per Aldehyde Group of 189 Daltons To a 3-L round bottom flask containing a magnetic stir bar was added 1.0 L of water and 10.0 g of the sodium salt of carboxymethylcellulose, average molecular weight of 90 kDa (Sigma, low viscosity, degree of carboxymethylation of 0.82). The mixture was stirred for 1 h at room temperature to form a clear solution, after which time a solution of sodium periodate in water (5.29 g of sodium periodate in 70 mL of water) was added drop-wise. The flask was covered with aluminum foil and the solution was stirred for 72 h. After this time, 78 mL of ethylene glycol was added to quench the reaction. The reaction mixture was dialyzed in regenerated cellulose dialysis membranes for 72 h. Lyophilization of the solution gave 9.2 g of white solid.

The weight-average molecular weight of the resulting oxidized CMC was determined to be 11 kDa using gel permeation chromatography (GPC). The dialdehyde content was determined to be 60% using the method described above (equivalent weight per aldehyde group of 189 Daltons). This oxidized carboxymethylcellulose is referred to herein as CMC-CHO-11-60.

Examples 1-12

Formation of Hydrogels from CMDX-NH2 and CMC-CHO

The purpose of these Examples was to demonstrate the preparation of hydrogels from reaction of a carboxymethyldextran derivatized to contain primary amines (CMDX-NH2) with oxidized carboxymethylcellulose containing aldehyde groups (CMC-CHO). The gel time to form the hydrogels was measured.

Into a small culture tube (14×150 mm), 100 µL of an aqueous CMDX-NH2 stock solution (20 wt %), as given in Table 1, was added. The vial was tilted and 100 µL of a 20 wt % aqueous CMC-CHO solution was added. A timer was immediately started and the two solutions were stirred together with the wooden end of a cotton swab. The gel time was defined as the time when stirring pulled the gel from the sides of the vial so that the gel could be removed as the wooden stirring rod was pulled from the vial.

The gel times are given in Table 1. The final gel times ranged from 7 to 32 s, depending on the oxidation conversion of the CMC-CHO and the amine substitution level of the CMDX-NH2.

TABLE 1

Gel Times for Hydrogels Formed from CMDX-NH2 and CMC-CHO

| Example | CMDX-NH2 (wt %) | CMC-CHO (wt %) | Gel Time (s) |
|---|---|---|---|
| 1 | CMDX-NH2-60-1.36-50.2 (20 wt %) | CMC-CHO-10.4-55 (20 wt %) | 10 |
| 2 | CMDX-NH2-60-1.36-50.2 (20 wt %) | CMC-CHO-10.4-55 (20 wt %) | 10 |
| 3 | CMDX-NH2-10-0.90-19 (20 wt %) | CMC-CHO-10.4-55 (20 wt %) | 9 |
| 4 | CMDX-NH2-60-0.91-15 (20 wt %) | CMC-CHO-10.4-55 (20 wt %) | 8 |
| 5 | CMDX-NH2-10-1.78-13 (20 wt %) | CMC-CHO-10.4-55 (20 wt %) | 8 |
| 6 | CMDX-NH2-60-1.8-33 (20 wt %) | CMC-CHO-10.4-55 (20 wt %) | 7 |
| 7 | CMDX-NH2-60-1.8-61 (20 wt %) | CMC-CHO-10.4-55 (20 wt %) | 9 |
| 8 | CMDX-NH2-60-1.8-61 (20 wt %) | CMC-CHO-28-23 (20 wt %) | 11 |
| 9 | CMDX-NH2-60-1.8-33 (20 wt %) | CMC-CHO-28-23 (20 wt %) | 32 |
| 10 | CMDX-NH2-60-1.8-61 (20 wt %) | CMC-CHO-20-62 (20 wt %) | 9 |
| 11 | CMDX-NH2-60-1.8-61 (18 wt %) | CMC-CHO-20-62 (20 wt %) | 11 |
| 12 | CMDX-NH2-10-1.78-73 (20 wt %) | CMC-CHO-11-60 (20 wt %) | 10 |

Examples 13-20

Measurement of In Vitro Degradation Time for CMDX-NH2/CMC-CHO Hydrogels

The purpose of these Examples was to demonstrate that the hydrogels formed by reaction of a CMDX-NH2 with a CMC-CHO degrade in vitro.

The hydrogel samples were prepared by mixing equal volumes of an aqueous solution of a CMDX-NH2 and an aqueous solution of a CMC-CHO through a 16 step mixing tip on a dual barrel syringe (Mixpac Systems AG (Rotkreuz, Switzerland). The compositions of the two aqueous solutions used are given in Table 2. After the hydrogels cured for 15 min, the samples were weighed and placed inside jars containing PBS at pH 7.4. The jars were placed inside a temperature-controlled shaker set at 80 rpm and 37° C. The samples were removed from the jars at various times, blotted to remove excess solution, and weighed. Then, the samples were returned to the jars.

The results are summarized in Table 2. The percent swell reported in the table is the weight of the hydrogel at the specified time divided by the initial weight of the hydrogel, multiplied by 100.

TABLE 2

Degradation Times for CMDX-NH2/CMC-CHO Hydrogels

| Example | CMDX-NH2 (wt %) | CMC-CHO (wt %) | Degradation time (h) |
|---|---|---|---|
| 13 | CMDX-NH2-60-1.36-50.2 (20 wt %) | CMC-CHO-10.4-55 (20 wt %) | 6 |
| 14 | CMDX-NH2-60-1.36-50.2 (20 wt %) | CMC-CHO-10.4-55 (20 wt %) | 6 |
| 15 | CMDX-NH2-60-1.8-33 (20 wt %) | CMC-CHO-10.4-55 (20 wt %) | 8 |
| 16 | CMDX-NH2-60-1.8-61 (20 wt %) | CMC-CHO-28-23 (20 wt %) | 4 |
| 17 | CMDX-NH2-60-1.8-33 (20 wt %) | CMC-CHO-28-23 (20 wt %) | 1 |
| 18 | CMDX-NH2-60-1.8-61 (20 wt %) | CMC-CHO-10.4-55 (20 wt %) | 9 |
| 19 | CMDX-NH2-60-1.8-61 (20 wt %) | CMC-CHO-20-62 (20 wt %) | 6 |
| 20 | CMDX-NH2-60-1.8-61 (20 wt %) | CMC-CHO-11-60 (20 wt %) | 2 |

These results demonstrate that the CMDX-NH2/CMC-CHO hydrogels tested degrade within 9 hours in the in vitro test. The degradation time was dependent on the particular combination of CMDX-NH2 and CMC-CHO used. In general, use of higher molecular weight CMDX-NH2 correlated with longer degradation time. In addition higher substitution levels for both components led to longer degradation times due to higher crosslink density.

Examples 21-25

Comparative

Measurement of In Vitro Degradation Time for CMDX-ADH/CMC-CHO Hydrogels

The purpose of these comparative Examples was to demonstrate that hydrogels formed by reacting a CMDX-ADH with a CMC-CHO, as described by Yeo et al. (copending U.S. Patent Application Publication No. 2008/0069857), degrade much more slowly than the hydrogels formed by reacting a CMDX-NH2 with a CMC-CHO, as disclosed herein. The CMDX-ADH/CMC-CHO hydrogels were prepared according to the methods described by Yeo et al. (U.S. Patent Application Publication No. 2008/0069857, Example 13). The degradation time of the hydrogels was determined using the in vitro test described in Examples 13-20.
Preparation of Carboxymethyldextrans Modified to Contain Hydrazide Groups
Preparation of 300 kDa Carboxymethyldextran Having a Degree of Carboxymethylation of 0.2 and a Hydrazide Substitution Level of 23% (CMDX-ADH-300-0.20-23)

The carboxymethyldextran modified with hydrazide groups was prepared using a two step procedure. The first step was to prepare a carboxymethyldextran having a weight-average weight of about 300 kDa and a degree of carboxymethylation of about 0.20 from dextran. In the second step, the carboxymethyldextran was modified to contain hydrazide groups by reaction with adipic dihydrazide.

Carboxymethyldextran having a weight-average molecular weight of about 300 kDa and a degree of carboxymethylation of about 0.20 was prepared as follows. To a 500-mL round bottom flask immersed in an ice bath was added 10 g of dextran having an average molecular weight of 400-500 kDa (Sigma) and 150 mL of water. To the solution was added 30.2 g of chloroacetic acid followed by 50 mL of 6 N NaOH. After the initial exotherm subsided, the reaction mixture was heated to 70° C. for 3.75 h, then cooled to room temperature, and the pH was adjusted to 7.0 with 6 N HCl. The reaction mixture was transferred to a glass jar and filtered using a Millipore Pellicon II TFF system. Five times the original volume of permeate was collected while continuously replacing with water. The final solution was lyophilized to give 9.25 g of white powder. The degree of carboxymethylation was found to be 0.20 by titration with standard NaOH using phenolphthalein as indicator. The weight-average molecular weight of the carboxymethyldextran product (CMDX-300-0.20) was found to be 300 kDa using GPC.

The carboxymethyldextran was modified to contain hydrazide groups as follows. To a 3-L round bottom flask equipped with overhead stirrer was added 4.5 g of CMDX-300-0.20) and 900 mL of water. The mixture was stirred until a clear solution was formed and then 30 equivalents (123.1 g) of adipic dihydrazide was added, forming a milky white suspension. Then, 370 mL of water was added to obtain a clear solution and the pH was adjusted to 6.8 with 0.25 N HCl. A solution of 12.7 g of hydroxybenzotriazole (Aldrich) in 57 mL of a 1:1 (v/v) mixture of DMSO and water was added, followed by addition of a solution of 18.1 g of EDC in 90 mL of a 1:1 (v/v) mixture of DMSO and water. The pH was adjusted to 6.8 with 0.25 N NaOH and then monitored every 15 min for 5 h and adjusted to maintain a pH of 6.8 by addition of 0.25 N HCl solution, as necessary. The reaction was then allowed to proceed for 12 h after which the pH was again adjusted to 6.8, and the entire reaction mixture was transferred to a glass jar. The Millipore Pellicon II TFF system was used to reduce the volume to about 300 mL and then filtration was continued, replacing the permeate with water until 1500 mL of additional permeate had been collected. The solution was then lyophilized to give a white solid (4.91 g). Analysis by $^1$H NMR, as described by Yeo, supra in Example 13, showed 23% incorporation of adipic dihydrazide groups. The resulting hydrazide modified carboxymethyldextran is referred to herein as CMDX-300-20-23.

Preparation of 282 kDa Carboxymethyldextran Having a Degree of Carboxymethylation of 0.80 and a Hydrazide Substitution Level of 71% (CMDX-ADH-285-0.80-71)

Carboxymethyldextran having a weight-average molecular weight of about 282 kDa and a degree of carboxymethylation of about 0.80 was prepared as follows. To a 500-mL round bottom flask immersed in an ice bath was added 10 g of dextran having an average molecular weight of 400-500 kDa (Sigma) and 150 mL of water. To the solution was added 30.2 g of chloroacetic acid, followed by 24 g of NaOH. After the initial exotherm subsided, the reaction mixture was heated to 70° C. for 3.75 h, then cooled to room temperature, and the pH was adjusted to 7.0 with 6 N HCl. The reaction mixture was transferred to a glass jar and filtered using a Millipore Pellicon II TFF system. Five times the original volume of permeate was collected while continuously replacing with water. The final solution was lyophilized to give 12.24 g of white powder. The degree of carboxymethylation was found to be 0.80 by titration with standard NaOH using phenolphthalein as indicator. The weight-average molecular weight of the carboxymethyldextran product (CMDX-282-0.80) was found to be 282 kDa using GPC.

The carboxymethyldextran was modified to contain hydrazide groups as follows. To a 3-L round bottom flask equipped with an overhead stirrer was added 10.15 g of CMDX-282-0.80 as prepared above, and 2000 mL of water. The mixture was stirred until a clear solution was obtained and then 30 equivalents (277.7 g) of adipic dihydrazide was added, forming a milky white suspension. Then, 650 mL of water was added to obtain a clear solution, and the pH was adjusted to 6.8 with 0.25 N HCl. A solution of 28.7 g of hydroxybenzotriazole (Aldrich) in 212 mL of a 1:1 (v:v) mixture of DMSO and water was added, followed by addition of a solution of 40.7 g of EDC in 127 mL of a 1:1 (v:v) mixture of DMSO and water. The pH was adjusted to 6.8 with 0.25 N NaOH and then monitored every 15 min for 5 h and adjusted to maintain a value of 6.8 by addition of 0.25 N HCl solution, as necessary. The reaction was allowed to proceed for 12 h, after which the pH was again adjusted to 6.8 and the entire contents was transferred to a glass jar. The Millipore Pellicon II TFF system was used to reduce the volume to about 300 mL and then filtration was continued with replacement of permeate with water until 1500 mL of additional permeate had been collected. The solution was then lyophilized to give a white solid (28.8 g). Analysis by $^1$H NMR, as described above, showed 71% incorporation of adipic dihydrazide groups. The resulting hydrazide modified carboxymethyldextran is referred to herein as CMDX-282-80-71.

Preparation of 130 kDa Carboxymethyldextran Having a Degree of Carboxymethylation of 0.79% and a Hydrazide Substitution Level of 69% (CMDX-ADH-130-0.79-69)

Carboxymethyldextran having a weight-average molecular weight of about 130 kDa and a degree of carboxymethylation of about 0.79 was prepared as follows. To a 3-L round bottom flask immersed in an ice bath was added 10 g of dextran having an average molecular weight of 64 to 94 kDa (Sigma) and 100 mL of water. To the solution was added 30.2 g of chloroacetic acid, followed by 24 g of NaOH pellets. After the initial exotherm subsided, the reaction mixture was heated to 70° C. for 2.5 h, cooled to room temperature, and the pH was adjusted to 7.0 with 6 N HCl. The reaction mixture was transferred to a glass jar and filtered using a Millipore Pellicon II TFF system. Five times the original volume of permeate was collected while continuously replacing with water. The final solution was lyophilized to give 9.44 g of white powder. The degree of carboxymethylation was found to be 79% by titration with standard NaOH using phenolphthalein as indicator. The weight-average molecular weight of the carboxymethyldextran product (CMDX-67-0.79) was determined to be 67 kDa using GPC.

The carboxymethyldextran was modified to contain hydrazide groups as follows. To a 3-L round bottom flask equipped with an overhead stirrer was added 3 g of CMDX-60-0.79 as prepared above, and 600 mL of water. The mixture was stirred until a clear solution was obtained and then 30 equivalents (139.2 g) of adipic dihydrazide was added, forming a milky white suspension. Then, 650 mL of water was added to obtain a clear solution, and the pH was adjusted to 6.8 with 0.25 N HCl. A solution of 14.4 g of hydroxybenzotriazole (Aldrich) in 101 mL of a 1:1 (v:v) mixture of DMSO and water was added, followed by addition of a solution of 20.4 g of EDC in 64.5 mL of a 1:1 (v:v) mixture of DMSO and water. The pH was adjusted to 6.8 with 0.25 N NaOH and then monitored every 15 min for 5 h and adjusted to maintain a pH value of 6.8 by addition of 0.25 N HCl solution, as necessary. The reaction was then allowed to proceed for 12 h, after which the pH was adjusted to 6.8 and the entire reaction mixture was transferred to a glass jar. The Millipore Pellicon II TFF system was used to reduce the volume to about 300 mL and then filtration was continued with replacement of permeate with water until 1500 mL of additional permeate had been collected. The solution was then lyophilized to give a white solid (3.35 g). Analysis by $^1$H NMR, as described above, showed 69% incorporation of adipic dihydrazide groups. The weight-average molecular weight was determined to be 130 kDa using GPC. The resulting hydrazide modified carboxymethyldextran is referred to herein as CMDX-130-0.79-69.

Preparation of Oxidized Carboxymethylcelluloses

Preparation of Oxidized Carboxymethyl Cellulose Having a Weight-Average Molecular Weight of 59 kDa and a Dialdehyde Content of 12% (CMC-CHO-59-12)

To a 3-L round bottom flask was added 20 g of carboxymethylcellulose (Sigma, low viscosity) and 2.0 L of water. The mixture was stirred for 2 h to form a clear solution and then a solution of 10.58 g of sodium periodate in 10 mL of water was added. The flask was covered with aluminum foil and the reaction mixture was stirred for 2 h. The reaction mixture was then transferred to a glass bottle and filtered on the Millipore Pellicon II TFF system, as described above, until 5× the original volume had been collected as permeate. The permeate was constantly replaced by addition of water. The solution was then lyophilized to give 18.6 g of white fluffy solid. The dialdehyde content was determined to be 12% using the titration method described above. The weight-average molecular weight was found to be 59 kDa by GPC. This oxidized carboxymethylcellulose is referred to herein as CMC-CHO-59-12.

Preparation of Oxidized Carboxymethylcellulose Having a Weight-Average Molecular Weight of 46 kDa and a Dialdehyde Content of 35% (CMC-CHO-59-12)

To a 3-L round bottom flask was added 20 g of carboxymethylcellulose (Sigma, low viscosity) and 2.0 L of water. The mixture was stirred for 2 h to form a clear solution and then a solution of 10.58 g of sodium periodate in 10 mL of water was added. The flask was covered with aluminum foil and the reaction mixture was stirred for 12 h. The reaction mixture was then transferred to a glass bottle and filtered on the Millipore Pellicon II TFF system, as described above, until 5× the original volume had been collected as permeate. The permeate was constantly replaced by addition of water. The solution was then lyophilized to give 8.6 g of white fluffy solid. The dialdehyde content was determined to be 35% using the titration method described above. The weight-average molecular weight was found to be 46 kDa by GPC. This oxidized carboxymethylcellulose is referred to herein as CMC-CHO-46-35.

Preparation of Oxidized Carboxymethyl Cellulose Having a Weight-Average Molecular Weight of 12 kDa and a Dialdehyde Content of 86% (CMC-CHO-12-86)

To a 3-L round bottom flask was added 4 g of carboxymethylcellulose (Sigma, low viscosity) and 400 mL of water. The mixture was stirred for 1 h to form a clear solution and then a solution of 2.11 g of sodium periodate in 30 mL of water was added. The flask was covered with aluminum foil and the reaction mixture was stirred for 64 h. The solution was transferred to a glass bottle and filtered on the Millipore Pellicon II TFF system, as described above, until 5× the original volume had been collected as permeate. The permeate was constantly replaced by addition of water. The solution was then lyophilized to give 3.58 g of white fluffy solid. The dialdehyde content was determined to be 86% using the titration method described above. The weight-average molecular weight was found to be 12 kDa by GPC. This oxidized carboxymethylcellulose is referred to herein as CMC-CHO-12-86.

Measurement of In Vitro Degradation Times

Hydrogels were prepared using the CMDX-ADH and CMC-CHO preparations described above using the method described in Examples 13-20. The compositions of the two aqueous solutions used are given in Table 3. The in vitro degradation times of the hydrogels was determined as described in Examples 1-13 and the results are given in Table 3.

TABLE 3

Degradation Times for CMDX-ADH/CMC-CHO Hydrogels

| Example | CMDX-ADH (wt %) | CMC-CHO (wt %) | Degradation Time (h) |
|---|---|---|---|
| 21, Comparative | CMDX-ADH-300-20-23 (4 wt %) | CMC-CHO-46-35 (6 wt %) | >240 |
| 22, Comparative | CMDX-ADH-300-20-23 (4 wt %) | CMC-CHO-59-12 (6 wt %) | >240 |
| 23, Comparative | CMDX-ADH-282-80-71 (4 wt %) | CMC-CHO-46-35 (6 wt %) | >240 |
| 24, Comparative | CMDX-ADH-282-80-71 (4 wt %) | CMC-CHO-59-12 (6 wt %) | >240 |
| 25, Comparative | CMDX-ADH-130-79-69 (6 wt %) | CMC-CHO-12-86 (6 wt %) | >270 |

The results demonstrate that the hydrogels formed by reaction of a hydrazide modified carboxymethyldextran with a carboxymethylcellulose dialdehyde that were tested have degradations times greater than 10 days in vitro. In comparison, hydrogels prepared from amine-containing carboxymethyldextran and carboxymethylcellulose dialdehyde degrade in vitro within 9 h, as shown in Examples 13-20.

Examples 26 and 27

In Vitro Biocompatibility Testing

Cytotoxicity

The purpose of these Examples was to demonstrate the safety of hydrogels resulting from the reaction of a CMDX-NH2 with a CMC-CHO in an in vitro test.

Mouse 3T3 fibroblast cell cultures were challenged with hydrogels made by combining equal volumes of an aqueous solution of a CMC-CHO and an aqueous solution of a CMDX-NH2, as shown in Table 4. A 30 mg sample of each hydrogel was placed into an empty well of a six-well culture plate. Mouse 3T3 fibroblast cells were then seeded into the well at a density of 50,000 cells per well. The plate was incubated at 37° C. for 24 h. Following the incubation, fibroblast cell growth and morphology were visualized directly, using a Nikon microscope with a 10× objective, equipped with a Nikon 35 mm camera. A visual cytotoxicity score was assigned according to a 5-point rating scale, ranging from 1=cytotoxic to 5=non-cytotoxic, based on observable characteristics of cell spreading and cell lysis. A score of 5 was assigned for a confluent monolayer of well-defined cells exhibiting cell-to-cell contact; cell morphology and cell density were not altered by the presence of a hydrogel and discrete intracytoplasmic granules were observed. No cell lysis was observed, indicating a non-cytotoxic reaction. A score of 4 was assigned when occasional lysed cells are present; not more than 20% of the cells appeared to be round, loosely attached, and without cytoplasmic granules. A score of 3 was assigned when cell lysis became more prevalent, but no more than 50% of the cells were round and devoid of intracytoplasmic granules. A score of 2 was assigned when the majority of cells were affected, but not more than 70% of the cells were rounded or lysed. A score of 1 was assigned when destruction and lysis of cells was nearly complete; considerable open areas between cells indicated that extensive cell lysis had occurred, indicating a cytotoxic reaction. These results, summarized in Table 3, demonstrate a lack of cytotoxicity of the hydrogels, as well as the lack of adhesion of cell cultures to the hydrogels.

TABLE 4

Cytotoxicity of CMDX-NH2/CMC-CHO Hydrogels

| Example | CMDX-NH2 (wt %) | CMC-CHO (wt %) | Rating |
|---|---|---|---|
| 26 | CMDX-NH2-60-1.8-33 (20 wt %) | CMC-CHO-28-23 (20 wt %) | 4.5 |
| 27 | CMDX-NH2-60-1.8-61 (20 wt %) | CMC-CHO-20-62 (20 wt %) | 4.5 |

Example 28

In Vivo Testing of Adhesion Prevention Using a Rabbit Side Wall Abrasion Model

The purpose of this Example was to demonstrate the effectiveness of a hydrogel formed from the reaction of a CMDX-NH2 with a CMC-CHO in preventing adhesions when applied to abdominal wall defects. The testing was done using a rabbit side wall abrasion model. Rabbits provide a suitable model for post-surgical adhesion prevention testing because it is known in the art that peritoneal adhesions can be induced in rabbits (Orita et al., *Int. J. Fertil.* 36:172-177, 1991; and Yeo et al., *Biomaterials* 27:4698-4705, 2006).

The testing was done using four adult New Zealand White Rabbits. Two of the rabbits were treated with sterile, normal saline solution (Vedco, St. Joseph, Mo.) to serve as a positive control, and two of the rabbits were treated with a hydrogel formed by reaction of an aqueous solution containing 17 wt % CMC-CHO-20-62 and an aqueous solution containing 20 wt % of CMDX-NH2-60-1.8-61. The aqueous solution containing the CMC-CHO-20-62 was sterilized by gamma irradiation and the aqueous solution containing the CMDX-NH2-60-1.8-61 was sterilized by filtration through a 0.45 µm filter, followed by irradiation with ultraviolet light for 12 h. The two were applied to the surgical site using a spray device. The spray device included a commercially available 5-mL double barrel syringe, plunger and pistons from MEDMIX SYSTEMS AG (Rotkreuz, Switzerland). It also included a nozzle attachment, syringe holder, a 0.2 µm filter, gas line, needle valve, pressure regulator and carbon dioxide gas supply tank. The nozzle attachment was secured to the distal end of the dual syringe and the syringe holder. The nozzle attachment created two fluid communication paths to the dual syringe, one for each barrel of the double barrel syringe. The nozzle attachment also created a gas communication path to the carbon dioxide gas supply tank through the 0.2 µm filter, gas line, needle valve, and pressure regulator. The nozzle attachment was configured so the liquids, when pushed by the plunger and pistons, moved from the double barrel syringe through individual nozzles, without contacting each other until leaving the perspective nozzles. Each nozzle was surrounded by an annulus of fast moving gas from the gas line, causing the liquids to break up into a spray as they exited the nozzles. The distal ends of the nozzles of each liquid component were parallel and approximately 0.080 inches (2 mm) apart. This spray device configuration caused the gas and the two adhesive components to readily mix into one stream approximately 0.5 inches (1.27 cm) from the end of the nozzles.

Metacam® (Meloxicam) (Boehringer-Ingelheim Vetmedica, Germany), 0.2 mg/kg was administered subcutaneously to each rabbit prior to surgery. All animals were administered a loading dose of the antibiotic Enrofloxacin® (Bayer AG, Germany), 5 mg/kg, on the day of surgery. On the day of surgery, each rabbit was pre-medicated with Glycopyrrolate (0.02 mg/kg, subcutaneously), approximately 15 min prior to anesthesia. Inhalation anesthesia was used (Isoflurane 5%) via facemask, which was attached to a veterinary anesthesia machine. Subsequent anesthesia was maintained with Isoflurane (2-5%). Ophthalmic lubricant was placed in the eyes of the anesthetized animal. An electric animal clipper was used to depilate the surgical site, and the area was vacuumed to remove clippings. The surgical site was prepared by wiping with alcohol or chlorhexidine solution, followed by a surgical scrub solution (2% chlorhexidine acetate or betadine surgical scrub). The anesthetized animal was delivered to the operating table and lactated Ringer's solution was administered intravenously at a rate of approximately 10 mL/kg per hour throughout the surgical procedure. Heart Rate, SPO2, ECG and temperature were monitored during surgery. The surgical site was prepared again by wiping with alcohol or chlorhexidine, followed by a surgical scrub solution (2% chlorhexidine acetate and/or betadine surgical scrub). A sterile surgical drape was then applied to the prepared area using aseptic technique.

A midline incision along the linea alba was made and the abdominopelvic contents were inspected. The cecum was identified, externalized, and abraded using a sterile surgical gauze bidirectionally for approximately 20-40 strokes until bleeding occurred. On the right lateral abdominal wall, a 3×4 cm defect comprising the parietal peritoneum and a layer of muscle (about 1 mm thick) was excised starting 1 cm from the midline. The area was abraded using the procedure described above and the material to be tested (i.e., either the saline solution or the CMDX-NH2 and CMC-CHO solutions) was applied to the defect. The abdominal wall was closed using a continuous and interrupted suture pattern. The subcutaneous tissue was closed using a simple continuous suture pattern. The skin was closed with sutures and tissue adhesive (Vetbond™ Tissue Adhesive, 3M Company, St. Paul, Minn.) Tegaderm™ Dressing (3M Corp., St. Paul, Minn.) was placed over the incision following completion of closure. All animals received Enrofloxacin 5 mg/kg intramuscularly twice daily for the first 48 h postoperatively. Metacam® (Meloxicam) 0.2 mg/kg was administered subcutaneously once daily for 3 days.

On day 7, all animals were euthanized with an intravenous injection of Euthasol® Euthanasia Solution (Virbac AH, Inc., Fort Worth, Tex.) via the marginal ear vein and the abdomen was opened, being careful not to disturb adhesions. The treatment application sites were exposed by cutting along the linea alba and making two lateral incisions approximately 10 cm cranial and caudal to defect. The condition of the application sites was documented photographically. The treatment application sites were assigned a score based on the presence of adhesions and the severity of the adhesions. Each implant site was assessed separately. Blunt dissection was utilized to remove and evaluate the severity of adhesions. The scoring was as follows:

Adhesion Extent Score, Estimation of Extent of Adhesions
0=no adhesions
1=1-25%
2=26-50%
3=51-75%
4=76-100%

Severity Score, Severity of Most Significant Adhesions
0=no adhesions
1=adhesion separated with minimal effort
2=adhesion separated with moderate effort
3=adhesion separated with difficulty The results are summarized in Table 5. As can be seen from the data in Table 5, the hydrogel formed by mixing an aqueous solution containing 17 wt % CMC-CHO-20-62 and an aqueous solution containing 20 wt % of CMDX-NH2-60-1.8-61 was more effective in preventing adhesions than the saline control. Specifically, no adhesions were detected in either rabbit treated with the hydrogel.

Macroscopic and microscopic analysis provided evidence that the hydrogel was not present at the site after 7 days.

TABLE 5

Adhesion and Severity Scores

| Treatment (n = 2 rabbits) | Average Adhesion Extent Score (0-4) | Average Severity Score (0-3) |
|---|---|---|
| Saline | 1.5 | 1.5 |
| 20 wt % CMDX-NH2-60-1.8-61/17 wt % CMC-CHO-20-62 | 0 | 0 |

What is claimed is:

1. A kit suitable for forming a tissue coating that is capable of preventing undesired tissue-to-tissue adhesions comprising:
   a) at least one carboxymethyldextran that has been derivatized to provide at least one aminocarboxymethyldextran that contains primary amine groups wherein each said primary amine group is directly bound to a primary, secondary or tertiary carbon atom, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; and
   b) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons.

2. The kit according to claim 1 wherein the degree of carboxymethylation of the carboxymethyldextran is about 0.9 to about 2.1.

3. The kit according to claim 1 wherein the weight-average molecular weight of the carboxymethyldextran is about 10,000 to about 60,000 Daltons.

4. The kit according to claim 1 wherein the primary amine substitution level of the aminocarboxymethyldextran is about 10% to about 75%.

5. The kit according to claim 1 wherein the weight-average molecular weight of the oxidized carboxymethylcellulose is about 10,000 to about 30,000 Daltons.

6. The kit according to claim 1 wherein the equivalent weight per aldehyde group of the oxidized carboxymethylcellulose is about 180 to about 495 Daltons.

7. The kit according to claim 1 wherein the aminocarboxymethyldextran is contained in a first aqueous solution or dispersion and the oxidized carboxymethylcellulose is contained in a second aqueous solution or dispersion.

8. The kit according to claim 7 wherein the first aqueous solution or dispersion contains the aminocarboxymethyldextran at a concentration of about 5% to about 50% by weight relative to the total weight of the solution or dispersion.

9. The kit according to claim 7 wherein the second aqueous solution or dispersion contains the oxidized carboxymethylcellulose at a concentration of about 5% to about 50% by weight relative to the total weight of the solution or dispersion.

10. The kit according to claim 7 wherein at least one of the first aqueous solution or dispersion or the second aqueous solution or dispersion further comprises at least one additive selected from the group consisting of pH modifiers, viscosity modifiers, antimicrobials, colorants, healing promoters, surfactants, pharmaceutical drugs and therapeutic agents.

11. The kit according to claim 1 wherein the aminocarboxymethyldextran and the oxidized carboxymethylcellulose are in the form of finely divided powders.

12. A dried hydrogel formed by a process comprising the steps of:
   a) reacting in a solvent (i) at least one carboxymethyldextran that has been derivatized to provide at least one aminocarboxymethyldextran that contains primary amine groups wherein said primary amine group is directly bound to a primary, secondary or tertiary carbon atom, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; with (ii) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons, to form a hydrogel; and
   b) treating said hydrogel to remove at least a portion of said solvent to form the dried hydrogel.

13. The dried hydrogel according to claim 12 wherein said dried hydrogel is in the form of a film.

14. The dried hydrogel according to claim 12 wherein said dried hydrogel is in the form of finely divided particles.

15. A method for forming a tissue coating that is capable of preventing undesired tissue-to-tissue adhesions comprising:
   applying to an anatomical site on tissue of a living organism:
   a) at least one carboxymethyldextran that has been derivatized to provide at least one aminocarboxymethyldextran that contains primary amine groups wherein said primary amine group is directly bound to a primary, secondary or tertiary carbon atom, said at least one carboxymethyldextran having a weight-average molecular weight of about 1,000 to about 1,000,000 Daltons, and a degree of carboxymethylation of about 0.1 to about 2.5, said at least one aminocarboxymethyldextran having a primary amine substitution level of about 10% to about 150%; followed by b) at least one carboxymethylcellulose that has been oxidized to provide at least one oxidized carboxymethylcellulose containing aldehyde groups, said at least one oxidized carboxymethylcellulose having a weight-average molecular weight of about 5,000 to about 100,000 Daltons, and an equivalent weight per aldehyde group of about 125 to about 750 Daltons;

or applying (b) followed by (a) and mixing (a) and (b) on the site;

or premixing (a) and (b) and applying the resulting mixture to the site.

* * * * *